United States Patent
Hildebrandt et al.

(10) Patent No.: US 7,108,977 B2
(45) Date of Patent: Sep. 19, 2006

(54) PROCESS FOR DETERMINING THE TUMORICIDAL POTENTIAL OF A SAMPLE THE USE OF A NUCLEIC ACID WHICH IS DOWNREGULATED IN HUMAN TUMOR CELLS

(75) Inventors: Tobias Hildebrandt, Reutlingen (DE); Goos van Muijen, Nijmegen (NL); Ulrich Weidle, München (DE)

(73) Assignee: Hoffmann-La Roche Inc., Nutley, NJ (US)

(*) Notice: Subject to any disclaimer, the term of this patent is extended or adjusted under 35 U.S.C. 154(b) by 460 days.

(21) Appl. No.: 10/276,566

(22) PCT Filed: May 17, 2001

(86) PCT No.: PCT/EP01/05627

§ 371 (c)(1),
(2), (4) Date: Mar. 19, 2003

(87) PCT Pub. No.: WO01/90353

PCT Pub. Date: Nov. 29, 2001

(65) Prior Publication Data

US 2004/0058337 A1    Mar. 25, 2004

(30) Foreign Application Priority Data

May 19, 2000 (EP) .................................. 00110692

(51) Int. Cl.
*C12Q 1/68* (2006.01)
(52) U.S. Cl. .......................................................... 435/6
(58) Field of Classification Search ...................... None
See application file for complete search history.

(56) References Cited

FOREIGN PATENT DOCUMENTS

| EP | 063 879 | 11/1982 |
|---|---|---|
| EP | 173 251 | 3/1986 |
| EP | 200 362 | 12/1986 |
| WO | WO 89/06698 | 7/1989 |
| WO | WO 98/39448 A2 * | 9/1998 |
| WO | WO 98/55508 A2 * | 12/1998 |
| WO | WO 99/46385 A2 * | 9/1999 |
| WO | WO 99/54461 A2 * | 10/1999 |
| WO | WO 00/55629 A2 * | 3/2000 |
| WO | WO 00/55350 A1 * | 9/2000 |
| WO | WO 00/61612 A2 * | 10/2000 |

OTHER PUBLICATIONS

Kennell, Progr. Nucl. Acid Res. Mol. Biol. 11: 259-301 (1971).*
Hildebrandt et al, Anticancer Res. 21: 1071 (2001).*
Hildebrandt et al, Anticancer Res. 20: 2801 (2000).*
van Muijen et al., Clin. Expl. Metastasis, 9, pp. 259-272 (1991).
Versteeg et al., EMBO J., 7, pp. 1023-1029 (1988).
Boraschi et al., Cell Immunol., 45, pp. 188-194 (1979).
Boraschi et al., J. Immunol, 131, pp. 1707-1713 (1983).

* cited by examiner

*Primary Examiner*—James Martinell
(74) *Attorney, Agent, or Firm*—George W. Johnston; Patricia S. Rocha-Tramaloni; Brian C. Remy

(57) ABSTRACT

A process for determining whether or not a cancer cell-containing test sample originating from or containing human cells has potential for tumor development, tumor progression or metastasis, wherein the test sample and a second sample originating from non-tumor cells obtained from the same individual or a different individual of the same species are analyzed by incubating each respective sample with a nucleic probe of sequence SEQ ID NO:1 and determining the approximate amount of hybridization of each respective sample with said probe, and comparing the approximate amount of hybridization of the test sample to an approximate amount of hybridization of said second sample to identify whether or not the test sample contains a greater amount of the specific nucleic acid or mixture of nucleic acids than does said second sample.

4 Claims, 7 Drawing Sheets

2.0 kb →

β-actin → paracentral gyrus

SEQUENCE LISTING

<160> NUMBER OF SEQ ID NOS: 10

<210> SEQ ID NO 1
<211> LENGTH: 1890
<212> TYPE: DNA
<213> ORGANISM: Homo sapiens
<220> FEATURE:
<221> NAME/KEY: CDS
<222> LOCATION: (38)..(616)
<220> FEATURE:
<221> NAME/KEY: modified_base
<222> LOCATION: (465)
<223> OTHER INFORMATION: c or g

<400> SEQUENCE: 1

```
ccgctccgct ccgctcggcc ccgcgccgcc cgtcaac atg atc cgc tgc ggc ctg      55
                                        Met Ile Arg Cys Gly Leu
                                        1               5 gcc tgc gag cgc tgc cgc tgg atc ctg ccc ctg ctc cta ctc agc gcc     103
Ala Cys Glu Arg Cys Arg Trp Ile Leu Pro Leu Leu Leu Leu Ser Ala
            10                  15                  20 atc gcc ttc gac atc atc gcg ctg gcc ggc cgc ggc tgg ttg cag tct     151
Ile Ala Phe Asp Ile Ile Ala Leu Ala Gly Arg Gly Trp Leu Gln Ser
        25                  30                  35 agc gac cac ggc cag acg tcc tcg ctg tgg tgg aaa tgc tcc caa gag     199
Ser Asp His Gly Gln Thr Ser Ser Leu Trp Trp Lys Cys Ser Gln Glu
    40                  45                  50 ggc ggc ggc agc ggg tcc tac gag gag ggc tgt cag agc ctc atg gag     247
Gly Gly Gly Ser Gly Ser Tyr Glu Glu Gly Cys Gln Ser Leu Met Glu
55                  60                  65                  70 tac gcg tgg ggt aga gca gcg gct gcc atg ctc ttc tgt ggc ttc atc     295
Tyr Ala Trp Gly Arg Ala Ala Ala Ala Met Leu Phe Cys Gly Phe Ile
                75                  80                  85 atc ctg gtg atc tgt ttc atc ctc tcc ttc ttc gcc ctc tgt gga ccc     343
Ile Leu Val Ile Cys Phe Ile Leu Ser Phe Phe Ala Leu Cys Gly Pro
            90                  95                 100 cag atg ctt gtc ttc ctg aga gtg att gga ggt ctc ctt gcc ttg gct     391
Gln Met Leu Val Phe Leu Arg Val Ile Gly Gly Leu Leu Ala Leu Ala
        105                 110                 115 gct gtg ttc cag atc atc tcc ctg gta att tac ccc gtg aag tac acc     439
Ala Val Phe Gln Ile Ile Ser Leu Val Ile Tyr Pro Val Lys Tyr Thr
    120                 125                 130 cag acc ttc acc ctt cat gcc aac cst gct gtc act tac atc tat aac     487
Gln Thr Phe Thr Leu His Ala Asn Xaa Ala Val Thr Tyr Ile Tyr Asn
135                 140                 145                 150 tgg gcc tac ggc ttt ggg tgg gca gcc acg att atc ctg aty ggc tgt     535
Trp Ala Tyr Gly Phe Gly Trp Ala Ala Thr Ile Ile Leu Ile Gly Cys
                155                 160                 165 gcc ttc ttc ttc tgc tgc ctc ccc aac tac gaa gat gac ctt ctg ggc     583
Ala Phe Phe Phe Cys Cys Leu Pro Asn Tyr Glu Asp Asp Leu Leu Gly
            170                 175                 180 aat gcc aag ccc agg tac ttc tac aca tct gcc taacttggga atgaatgtgg   636
Asn Ala Lys Pro Arg Tyr Phe Tyr Thr Ser Ala
        185                 190 gagaaaatcg ctgctgctga gatggactcc agaagaagaa actgtttctc caggcgactt   696
tgaacccatt ttttggcagt gttcatatta ttaaactagt caaaaatgct aaaataattt   756
gggagaaaat attttttaag tagtgttata gtttcatgtt tatcttttat tatgttttgt   816
gaagttgtgt cttttcacta attacctata ctatgccaat atttcctat atctatccat    876
```

```
aacatttata ctacatttgt aagagaatat gcacgtgaaa cttaacactt tataaggtaa      936
aaatgaggtt tccaagattt aataatctga tcaagttctt gttatttcca aatagaatgg      996
actcggtctg ttaagggcta aggagaagag gaagataagg ttaaaagttg ttaatgacca     1056
aacattctaa aagaaatgca aaaaaaaagt ttattttcaa gccttcgaac tatttaagga     1116
aagcaaaatc atttcctaaa tgcatatcat ttgtgagaat ttctcattaa tatcctgaat     1176
cattcatttc agctaaggct tcatgttgac tcgatatgtc atctaggaaa gtactatttc     1236
atggtccaaa cctgttgcca tagttggtaa ggctttcctt taagtgtgaa atatttagat     1296
gaaattttct cttttaaagt tctttatagg gttagggtgt gggaaaatgc tatattaata     1356
aatctgtagt gttttgtgtt tatatgttca gaaccagagt agactggatt gaaagatgga     1416
ctgggtctaa tttatcatga ctgatagatc tggttaagtt gtgtagtaaa gcattaggag     1476
ggtcattctt gtcacaaaag tgccactaaa acagcctcag gagaataaat gacttgcttt     1536
tctaaatctc aggtttatct gggctctatc atatagacag gcttctgata gtttgcaact     1596
gtaagcagaa acctacatat agttaaaatc ctggtctttc ttggtaaaca gatttttaaat     1656 gtctgatata aaacatgcca caggagaatt cggggatttg agtttctctg aatagcatat     1716
atatgatgca tcggataggt cattatgatt ttttaccatt tcgacttaca taatgaaaac     1776
caattcattt taaatatcag attattattt tgtaagttgt ggaaaaagct aattgtagtt     1836
ttcattatga agttttccca ataaaccagg tattctaaaa aaaaaaaaaa aaaa          1890
```

<210> SEQ ID NO 2
<211> LENGTH: 193
<212> TYPE: PRT
<213> ORGANISM: Homo sapiens
<220> FEATURE:
<221> NAME/KEY: MOD_RES
<222> LOCATION: (143)
<223> OTHER INFORMATION: Pro or Arg

<400> SEQUENCE: 2

```
Met Ile Arg Cys Gly Leu Ala Cys Glu Arg Cys Arg Trp Ile Leu Pro
  1               5                  10                  15

Leu Leu Leu Leu Ser Ala Ile Ala Phe Asp Ile Ile Ala Leu Ala Gly
             20                  25                  30

Arg Gly Trp Leu Gln Ser Ser Asp His Gly Gln Thr Ser Ser Leu Trp
         35                  40                  45

Trp Lys Cys Ser Gln Glu Gly Gly Ser Gly Ser Tyr Glu Glu Gly
     50                  55                  60

Cys Gln Ser Leu Met Glu Tyr Ala Trp Gly Arg Ala Ala Ala Met
 65                  70                  75                  80

Leu Phe Cys Gly Phe Ile Ile Leu Val Ile Cys Phe Ile Leu Ser Phe
                 85                  90                  95

Phe Ala Leu Cys Gly Pro Gln Met Leu Val Phe Leu Arg Val Ile Gly
                100                 105                 110

Gly Leu Leu Ala Leu Ala Ala Val Phe Gln Ile Ile Ser Leu Val Ile
            115                 120                 125

Tyr Pro Val Lys Tyr Thr Gln Thr Phe Thr Leu His Ala Asn Xaa Ala
        130                 135                 140

Val Thr Tyr Ile Tyr Asn Trp Ala Tyr Gly Phe Gly Trp Ala Ala Thr
145                 150                 155                 160

Ile Ile Leu Ile Gly Cys Ala Phe Phe Phe Cys Cys Leu Pro Asn Tyr
                165                 170                 175
```

-continued

Glu Asp Asp Leu Leu Gly Asn Ala Lys Pro Arg Tyr Phe Tyr Thr Ser
            180                 185                 190
Ala

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:primer
      312rev1

<400> SEQUENCE: 3
aaatccccga attctcctgt gg                                           22

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:primer 312f6

<400> SEQUENCE: 4
acccgctccg ctccgctc                                                18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:forward
      primer

<400> SEQUENCE: 5
tccttcccac ctcccttct                                               19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:reverse
      primer

<400> SEQUENCE: 6
taagaactaa agttgcctgt tc                                           22

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:forward
      primer

<400> SEQUENCE: 7
caactggatt caaaatagat gtc                                          23

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:reverse
      primer

<400> SEQUENCE: 8

```
atggcagcag gctatgt                                                   17

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:forward
      primer

<400> SEQUENCE: 9
atgtcctcat tggtgttgtg                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:reverse
      primer

<400> SEQUENCE: 10
gattcagagc ccaggaagat                                                20
```

PROCESS FOR DETERMINING THE TUMORICIDAL POTENTIAL OF A SAMPLE THE USE OF A NUCLEIC ACID WHICH IS DOWNREGULATED IN HUMAN TUMOR CELLS

Carcinogenesis, tumor progression and metastasis result from an imbalanced transcriptional program, inappropriate post-translational modifications and deregulated epigenetic modifications (Schwirzke, M. et al., Anticancer Res 19 (1999) 1801–1814; Pardee, A. B., Advances in Cancer Res 65 (1994) 213–227; Ponta, H., Biochim Biophys Acta 1198 (1994) 1–10). Changes of the transcriptional program are due to oncogenes and tumor suppressor genes, fusion proteins created by cytogenetic alterations, altered expression of genes due to unscheduled methylation by DNA methyltransferases and chromatin modifying enzymes such as histone acetyltransferases and histone deacetylases (Lin, R. J. et al., Trends Genet 15 (1999) 179–184; Stunnenberg, H. G. et al., Biochim Biophys Acta 1423 (1999) F15–F33).

For identification of tumor-related candidate genes, transcriptional profiling of cellular systems such as metastasizing versus non-metastasizing cell lines and tumor specimen corresponding to different stages of progression is the first step for achievement of this goal (Schiemann, S. et al., Anticancer Research 17 (1997) 13–20; Schwirzke, M. et al., Anticancer Research 18 (1998) 1409–1422; Schiemann, S. et al., Clin Exp Metastasis 16 (1998) 129–139). Further steps involve analysis of prevalence of the identified alteration in different tumors, in-vitro modulation of the gene under consideration by overexpression and downregulation making use of antisense RNA or ribozymes in stable transfectants and assessing the consequences in relevant in-vitro systems. The advent of nude mouse systems, including subcutaneous xenograft systems and orthotopic implantation in which the natural tropism of metastasis of the tumor under investigation is maintained, has paved the way for assessment of the functional role of candidate genes in vivo (Fidler, I. J., Cancer Metastasis Rev 50 (1986) 29–49).

Loss of heterozygosity (LOH) at critical chromocal loci is associated with a higher risk of cancer development. LOH at such critical loci may be used as a valuable marker to determine the potential of cancer development in early stages and to evaluate the efficacy of chemopreventive and chemotherapeutic agents. The genes located on chromosome 6q are extremely polymorphic and provide for a natural heterozygous gene system. LOH on chromosome 6q indicates a high probability of tumor development such as malignant melanoma (Healy, E. et al., Oncogene 16 (1998) 2213–2218; Robertson, G. P. et al., Cancer Res 56 (1996) 1635–1641; Ray, M. E. et al., Oncogene 12 (1996) 2527–2533; Millikin, D. et al., Cancer Research 51 (1991) 5449–5453), pancreatic cancer (Griffin, C. A. et al., Cancer Research 55 (1995) 2394–2399; cervical cancer (Huettner, P. C. et al., Human Pathol 29 (1998) 364–370) prostate cancer (Srikantan, V. et al., Int J Cancer 84 (1999) 331–335; MacGrogan, D. and Bookstein, R., Seminars in Cancer Biology 8 (1997) 11–19; Verma, R. S. et al., Cancer Investigation 17 (1999) 441–447) and breast cancer (Bilanges, B. et al., Oncogene 18 (1999) 3979–3988; Chappell, S. A. et al., British J Cancer 75 (1997) 1324–1329; Devilee, P., et al., Oncogene 6 (1991) 1705–1711; Noviello, C. et al., Clin Cancer Research 2 (1996) 1601–1606; Fujii, H., et al., Genes, Chromosomes & Cancer 16 (1996) 35–39).

SUMMARY OF INVENTION

The present invention provides a process for detecting the presence or absence of at least one specific nucleic acid or mixture of nucleic acids, or distinguishing between two different sequences in a sample, wherein the sample is suspected of containing said sequence or sequences, which process comprises the following steps in order:
(a) incubating said sample under stringent hybridization conditions with a nucleic acid probe which is selected from the group consisting of:
  (i) a nucleic acid sequence of SEQ ID NO: 1;
  (ii) a nucleic acid sequence which is complementary to the nucleic acid sequence of (i);
  (iii) a nucleic acid sequence which hybridizes under stringent conditions with the sequence of (i); and
  (iv) a nucleic acid sequence which hybridizes under stringent conditions with the sequence of (ii); and
(b) determining whether said hybridization has occurred.

Moreover, the present invention provides a process for determining whether or not a test sample originating from or containing human cells, preferably a test sample originating from or containing epithelial cells, has potential for tumor development, progression or metastasis of said cells, wherein the test sample and a second sample originating from non-tumor cells from the same individual or a different individual of the same species is analyzed by:
(a) incubating the respective sample under stringent hybridization conditions with a nucleic acid probe which is selected from the group consisting of:
  (i) a nucleic add sequence of SEQ ID NO: 1;
  (ii) a nucleic acid sequence which is complementary to the nucleic add sequence of (i);
  (iii) a nucleic acid sequence which hybridizes under stringent conditions with the sequence of (i); and
  (iv) a nucleic acid sequence which hybridizes under stringent conditions with the sequence of (ii); and
(b) determining the approximate amount of hybridization of each respective sample with said probe, and
(c) comparing the approximate amount of hybridization of the test sample to an approximate amount of hybridization of said second sample to identify whether or not the test sample contains a greater amount of the specific nucleic add or mixture of nucleic acids than does said second sample.

DETAILED DESCRIPTION OF THE INVENTION

The present invention provides the use of the THW gene for diagnostics, especially in the field of cancer. In particular, the invention involves the identification and the measurement of the amount of expression of said gene THW in mammalian, especially in malignant tumor cells. The invention also relates to diagnosis of the metastatic and progression potential of tumor cells.

THW nucleic acid has downregulated expression in tumor cells and is capable of suppressing tumor progression and/or metastasis, especially in malignant melanoma and mammary carcinoma cells.

A tumor suppressor gene named THW is located on chromosome 6q and its loss or inhibition is correlated with a tumor potential. Also a protein, termed THW, is provided which is downregulated in cancer cells as compared to their non-cancerous counterparts. THW may be involved in tumor suppression and especially in suppression of metastasis. The THW gene codes for a polypeptide of SEQ ID NO:2.

The nucleic acid encoding THW protein is downregulated in tumor cells and can be selected from the group consisting of:

(a) SEQ ID NO: 1;
(b) a nucleic acid sequence which hybridizes under stringent conditions with a nucleic acid probe of the complementary sequence of (a),
(c) a nucleic acid sequence which, because of the degeneracy of the genetic code, is not a sequence of (a) or (b), but which codes for a polypeptide having exactly the same amino acid sequence as a polypeptide encoded by a sequence of (a) or (b); and
(d) a nucleic acid sequence which is a fragment of any of the sequences of (a), (b) or (c).

THW polypeptide is encoded by a nucleic acid selected from the group consisting of:

(a) SEQ ID NO: 1;
(b) a nucleic acid sequence which hybridizes under stringent conditions with a nucleic acid probe of the complementary sequence of (a);
(c) a nucleic acid which is a fragment of any of the sequences of (a) or (b).

Preferably, THW polypeptide has the sequence of SEQ ID NO:2.

The isolated THW polypeptide and, thus, its encoding nucleic acid can occur in natural allelic variations which differ from individual to individual. Such variations of the amino acids are usually amino acid substitutions. However, they may also be deletions, insertions or additions of amino adds to the total sequence. The THW protein according to the invention—depending, both in respect of the extent and type, on the cell and cell type in which it is expressed—can be in glycosylated or non-glycosylated form. Polypeptides with tumor suppressor activity can be identified by transfection of THW-negative tumor cells with expression vectors for THW, establishment of stable transfectants and evaluation of their tumoricidal capacity after xenografting into nude mice. Such evaluation can be performed, e.g., according to Boraschi, D., et al., Cell Immunol. 45 (1979) 188–194 and Boraschi, D., et al., J. Immunol. 131 (1983) 1707–1713.

"Polypeptide with THW activity or THW" means also proteins with minor amino acid variations but with substantially the same THW activity. Substantially the same means that the activities are of the same biological properties and the polypeptides show at least 90% identity in amino acid sequence.

The term "nucleic acid molecule or nucleic acid" denotes a polynucleotide molecule which can be, for example, a DNA, RNA, or derivatized active DNA or RNA. DNA and/or RNA molecules are preferred, however.

The term "hybridize under stringent conditions" means that two nucleic acid fragments are capable of hybridization to one another under standard hybridization conditions described in Sambrook et al., Molecular Cloning: A Laboratory Manual (1989) Cold Spring Harbor Laboratory Press, New York, USA. More specifically, "stringent conditions" as used herein refer to hybridization in 6.0×SSC at about 45° C., followed by a wash. This wash can be with 2.0×SSC at 50° C. Preferably, hybridization is performed using the commercially available Express Hyb™ Hybridization Solution of Clontech, which is a non-viscous solution containing no salmon sperm DNA. The stringency of the salt concentration in the wash step can be selected, for example, from about 2.0×SSC at 50° C., for low stringency, to about 0.2×SSC at 50° C., for high stringency. In addition, the temperature in the wash step can be increased from low stringency conditions at room temperatures, about 22° C., to high stringency conditions at about 65° C.

The phrase "nucleic acid or polypeptide" as used throughout this application refers to a nucleic acid or polypeptide having a THW activity which is substantially free of cellular material or culture medium when produced by recombinant DNA techniques, or substantially free of chemical precursors or other chemicals when synthesized chemically. Such a nucleic acid is preferably free of sequences which naturally flank the nucleic acid (i.e. sequences located at the 5' and the 3' ends of the nucleic acid) in the organism from which the nucleic acid is derived.

THW can be purified after recombinant production by affinity chromatography using known protein purification techniques, including immunoprecipitation, gel filtration, ion exchange chromatography, chromatofocussing, isoelectric focussing, selective precipitation, electrophoresis, or the like.

The polypeptides according to the invention can be produced by recombinant means, or synthetically. Non-glycosylated THW polypeptide is obtained when it is produced recombinantly in prokaryotes. With the aid of the nucleic acid sequences provided by the invention it is possible to search for the THW gene or its variants in genomes of any desired cells (e.g. apart from human cells, also in cells of other mammals), to identify these and to isolate the desired gene coding for the THW protein. Such processes and suitable hybridization conditions are known to a person skilled in the art and are described, for example, by Sambrook et al., Molecular Cloning: A Laboratory Manual (1989), Cold Spring Harbor Laboratory Press, New York, USA and Hames, B. D., Higgins, S. G., Nucleic Acid Hybridisation—A Practical Approach (1985) IRL Press, Oxford, England. In this case the standard protocols described in these publications are usually used for the experiments.

With the aid of such nucleic acids coding for a THW protein, the protein according to the invention can be obtained in a reproducible manner and in large amounts. For expression in prokaryotic or eukaryotic organisms, such as prokaryotic host cells or eukaryotic host cells, the nucleic acid is integrated into suitable expression vectors, according to methods familiar to a person skilled in the art. Such an expression vector preferably contains a regulatable/inducible promoter. These recombinant vectors are then introduced for the expression into suitable host cells such as, e.g., E. coli as a prokaryotic host cell or Saccharomyces cerevisiae, Teratocarcinoma cell line PA-1 sc 9117 (Büttner, R., et al., Mol. Cell. Biol. 11 (1991) 3573–3583), insect cells, CHO or COS cells as eukaryotic host cells and the transformed or transduced host cells are cultured under conditions which allow expression of the heterologous gene. The isolation of the protein can be carried out according to known methods from the host cell or from the culture supernatant of the host cell. Such methods are described for example by Ausubel I., Frederick M., Current Protocols in Mol. Biol. (1992), John Wiley and Sons, New York Also in vitro reactivation of the protein may be necessary if it is not found in soluble form in the cell culture.

The invention further comprises recombinant expression vectors which are suitable for the expression of THW, recombinant host cells transfected with such expression vectors, as well as a process for the recombinant production of a protein which is encoded by the THW gene.

The invention further comprises a method for detecting a nucleic acid molecule of gene THW, comprising incubating a sample (e.g., body fluids such as blood, cell lysates or DNA made by reverse transcription of sample RNA) with the isolated nucleic acid molecule according to the invention and determining hybridization under stringent conditions of said isolated nucleic acid molecule to a target nucleic acid molecule for determination of presence of a nucleic acid molecule which is the THW gene and therefore a method for the identification of the metastatic potential and/or progression of tumor cells.

To determine whether a cancer cell-containing test sample has potential for tumor development, progression or metastasis, the approximate amount of hybridization of the isolated nucleic acid with the target nucleic acid or nucleic acids is determined. The approximate amount of hybridization need not be determined quantitatively, although a quantitative determination is encompassed by the present invention. Typically, the approximate amount of hybridization is determined qualitatively, for example, by a sight inspection upon detecting hybridization. For example, if a gel is used to resolve labelled nucleic acid which hybridizes to target nucleic acid in the sample, the resulting band can be inspected visually. One can compare the approximate amount of hybridization in the test sample to the approximate amount of hybridization in non-tumor cells. Such non-tumor cells are, e.g., epithelial cells or peripheral blood cells.

As is shown in accordance with the present invention, the THW nucdeic acid is present in a lower amount in a tumor sample than in a sample free from peripheral blood cells of a healthy donor. A test sample having no or low potential for tumor progression or for metastasis will have a higher amount of the THW nucleic acid of the present invention than does a cancer cell sample which has a high tumor progression potential or a metastatic potential.

On the basis of the nucleic acids provided by the invention it is possible to provide a tumor test which uses the detection of THW nucleic acids as a measure of early tumor detection.

Methods of hybridization of a probe and a nucleic acid are known to a person skilled in the art and are described, for example, in WO 89/06698, EP-A 0 200 362, U.S. Pat. No. 2,915,082, EP-A 0 063 879, EP-A 0 173 251, EP-A 0 173 251.

In a preferred embodiment of the invention the nucleic acid of the sample is amplified before the test (and reverse-transcribed if the sample nucleic acid is RNA), for example by means of the known PCR technique. Usually a derivatized (labeled) nucleic acid probe is used within the framework of nucleic acid diagnostics. This probe is contacted with a denatured DNA or RNA from the sample which is bound to a carrier and in this process the temperature, ionic strength, pH and other buffer conditions are selected—depending on the length and composition of the nucleic acid probe and the resulting melting temperature of the expected hybrid—such that the labeled DNA or RNA can bind to homologous DNA or RNA (hybridization see also Wahl, G. M., et al., Proc. Natl. Acad. Sci. USA 76 (1979) 3683–3687). Suitable carriers are membranes or carrier materials based on nitrocellulose (e.g., Schleicher and Schüll, BA 85, Amersham Hybond, C.), strengthened or bound nitrocellulose in powder form or nylon membranes derivatized with various functional groups (e.g., nitro groups) (e.g., Schleicher and Schüll, Nytran; NEN, Gene Screen; Amersham Hybond M.; Pall Biodyne).

Preferably the nucleic acid probe is incubated with the nucleic acid of the sample and the hybridization is detected optionally by means of a further binding partner for the nucleic acid of the sample and/or the nucleic acid probe.

Hybridizing DNA or RNA can be detected by incubating the carrier with an antibody or antibody fragment after thorough washing and saturation to prevent unspecific binding. The antibody or the antibody fragment is directed towards the substance incorporated during hybridization to the nucleic acid probe. The antibody is in turn labeled. However, it is also possible to use a directly labeled DNA. After incubation with the antibodies it is washed again in order to only detect specifically bound antibody conjugates. The determination is then carried out according to known methods by means of the label on the antibody or the antibody fragment.

The detection of the expression can be carried out for example as:
  in situ hybridization with fixed whole cells, with fixed tissue smears,
  colony hybridization (cells) and plaque hybridization (phages and viruses),
  Southern hybridization (DNA detection),
  Northern hybridization (RNA detection),
  serum analysis (e.g., cell type analysis of cells in the serum by slot-blot analysis),
  after amplification (e.g., PCR technique).

The nucleic acids according to the invention are hence valuable prognostic markers in the diagnosis of the development and progression potential of tumors.

The invention further comprises a method for producing a protein whose expression is correlated with tumor suppression, by expressing an exogenous DNA in prokaryotic or eukaryotic host cells and isolation of the desired protein, wherein the protein is coded by the nucleic acid molecules according to the invention, preferably by the DNA sequence shown in SEQ ID NO:1.

The protein can be isolated from the cells or the culture supernatant and purified by chromatographic means, preferably by ion exchange chromatography, affinity chromatography and/or reverse phase HPLC.

The invention further comprises an isolated protein according to the invention which is encoded by a nucleic acid molecule according to the invention, preferably having the nucleotide sequence set forth in SEQ ID NO:1.

The present invention relates to the cloning and characterization of the gene THW, which is especially characterized as a tumor suppression gene, and as a downregulated gene indicative of tumorigenic potential.

According to the invention there are provided methods for identifying and isolation of compounds which have utility in the treatment of cancer, especially in tumor suppression. These methods include methods for modulating the expression of the polypeptides according to the invention, methods for identifying compounds which can mimic the proteins according to the invention, and methods of identifying compounds which can activate said polypeptides and the encoding genes. The methods further include methods for activating the transcription of THW gene to mRNA, which preferably downregulates the tumoricidal potential in a tumor cell. These methods can be conducted in vitro or in vivo and may make use of and establish cell lines and transgenic animal models of the invention.

THW activity may be measured in several ways. For example, the activation is apparent by a change in cell physiology, such as increased mobility and invasiveness in vitro, or by a change in the differentiation state, or by a change in cell metabolism leading to an increase of proliferation.

The THW gene is located on chromosome 6q, a region for which LOH has been found in several tumors, such as malignant melanoma (Healy, E. et al., Oncogene 16 (1998) 2213–2218; Robertson, G. P. et al., Cancer Res 56 (1996) 1635–1641; Trent, J. M. et al., Science 247 (1990) 568–71; Ray, M. E. et al., Oncogene 12 (1996) 2527–2533; Millikin, D. et al., Cancer Research 51 (1991) 5449–5453), pancreatic cancer (Griffin, C. A. et al., Cancer Research 55 (1995)

2394–2399), cervical cancer (Huettner, P. C., et al., Human Pathol 29 (1998) 364–370), prostate (Srikantan, V. et al., Int J Cancer 84 (1999) 331–335; MacGrogan, D. and Bookstein, R., Seminars in Cancer Biology 8 (1997) 11–19; Verma, R. S. et al., Cancer Investigation 17 (1999) 441–447) and breast cancer (Bilanges, B., Oncogene 18 (1999) 3979–3988; Chappell, S. A. et al., British J Cancer 75 (1997) 1324–1329; Devilee, P., et al., Oncogene 6 (1991) 1705–1711; Noviello, C. et al., Clin Cancer Research 2 (1996) 1601–1606; Fujii, H., et al., Genes, Chromosomes & Cancer 16 (1996) 35–39). The location of THW gene on chromosome 6q is within the interval D6S472-D6S453.

Loss of heterozygosity (LOH) in the THW gene can be detected according to the state of the art preferably with POR using microsatellite markers located in the above-mentioned interval. For the detection of LOH and status of microsatellite instability (MSI) determination primers (markers) from this interval and/or primers from the flanking intervals D6S434-D6S302 and D6S453-D6S311 can be used. Microsatellite markers within the intervals mentioned can be found in the Genome Database GDB. MSI detection can occur, using primers from the above-mentioned flanking regions, according to known methods as described, for example, by de la Chapelle, A., Eur. J. Hum. Genet. 7 (1999) 407–408 and Potocnik U. et al., Pflugers Arch 439 (3.sup.rd Suppl.) 2000, R47-9. Methods of LOH detection are described, for example, by Friedrich, M. G., et al., J. Urol. 163 (2000) 1039–1042; Sugano, K., et al., Genes, Chromosomes & Cancer 15 (1996) 157–164; Chen, Y. H., et al., J. Pathol. 177 (1995) 129–134; Hahn, M., et al., BioTechniques 18 (1995) 1040–1047; Lopez-Crapez, E., et al., BioTechniques 17 (1994) 1072–1 074, 1076; Dockhorn-Dworniczak, B., et al., Virchows Arch. 424 (1994) 337–342; Gruis, N. A., et al., Br. J. Cancer 68 (1993) 208–213; Merlo, G. R., et al., BioTechniques 11(1991)166–168, 170–171.

Preferably, higher molecular weight DNA is isolated from paraffin sections or from other tissue samples. Analysis is performed by PCR using oligonucleotides flanking polymorphic microsatellite markers containing dinucleotide repeats.

The following examples, references, sequence listing and figures are provided to aid the understanding of the present invention. It is understood that modifications can be made in the procedures set forth without departing from the spirit of the invention.

```
SEQ ID NO:1:     cDNA and amino acid sequence of
                 THW.
SEQ ID NO:2:     Amino acid of THW.
SEQ ID NO:3:     Primer 312rev1.
SEQ ID NO:4:     Primer 312f6.
SEQ ID NOS:5–10: Primer
```

Figure 1:
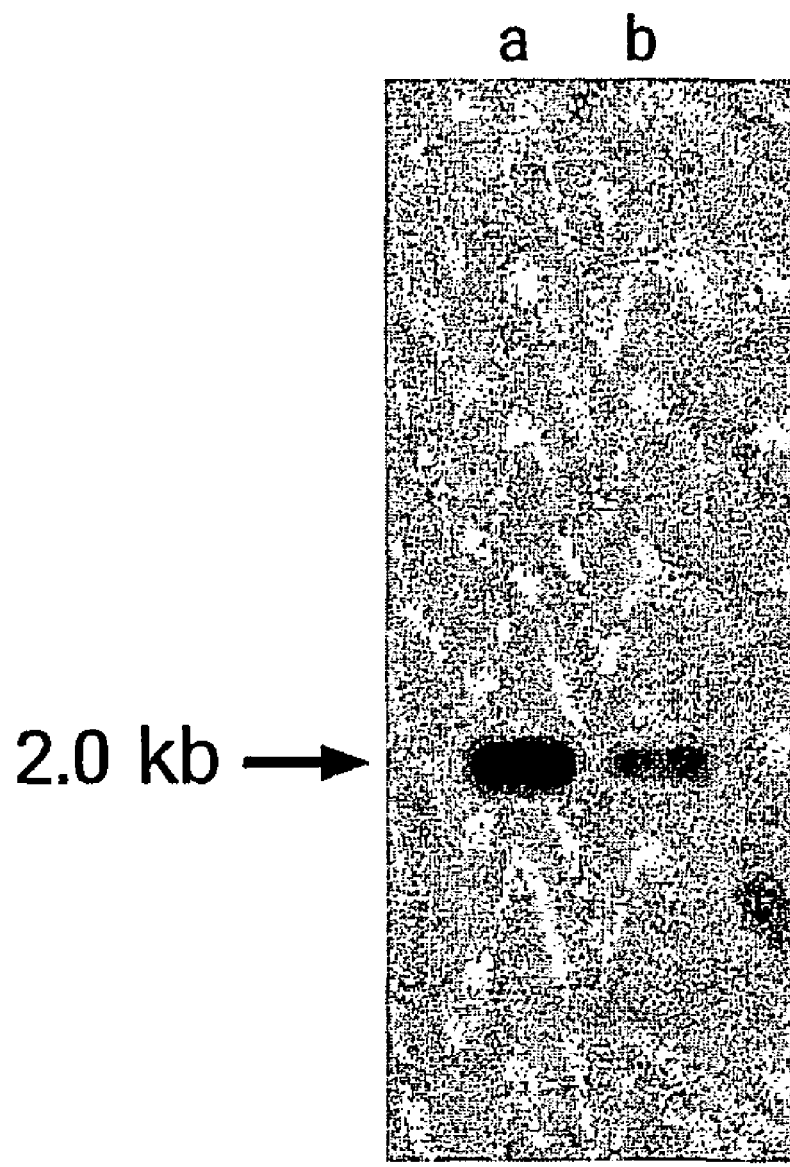
FIG. 1 Differential expression of the THW gene in cell lines 530 and NMCL-1.
RNA was size-separated on a 1% agarose-formaldehyde gel and hybridized to $\alpha\text{-}^{32}$P-labelled probe derived from THW cDNA as described in the Material and Methods section.
Lane a: cell line 530; lane b: cell line NMCL-1
Figure 1:
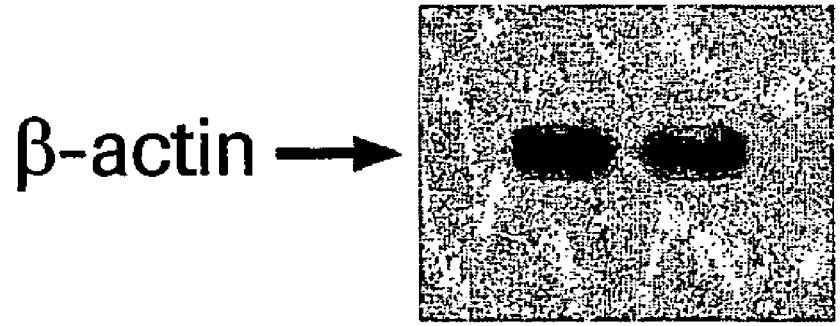

C1=frontal lobe; C2=corpus callosum; C3=thalamus; C4=atrium, left; C5=duodenum; C6=rectum; C7=spleen; C8=bladder;
C9=adrenal gland; C10=leukemia, K-562; C11=fetal kidney,
C12=E.coli rRNA.
D1=parietal lobe; D2=amygdala; D3=pituitary gland; D4=atrium, right; D5=jejunum; D7=thymus; D8=uterus; D9=thyroid gland;
D10=leukemia, MOLT-4; D11=fetal liver; D12=E.coli DNA.
E1=occipital lobe; E2=caudate nucleus; E3=spinal cord; E4=ventricle, left; E5=ileum; E7=peripheral blood leukocyte;
E8=prostate; E9=salivary gland; E10=Burkitt's lymphoma, Raji;
E11=fetal spleen; E12=Poly r(A).
F1=temporal lobe; F2=hippocampus; F4=ventricle, right; F5=ilocecum; F7=lymph node; F8=testis; F9=mammary gland;
F10=Burkitt's lymphoma, Daudi; F11=fetal thymus; F12=human $C_o$t-1 DNA.
G1=paracental gyrus of cerebral cortex; G2=medulla oblongata;
G4=interventricular septum; G5=appendix; G7=bone marrow;
G8=ovary; G10=colorectal adenocarcinoma SW480; G11=fetal lung; G12=human DNA 100 ng.
H=pons; H2=putamen; H4=apex of the heart; H5=colon, ascending; H7=trachea; H10=lung carcinoma, A549; H12=human DNA 500 ng.

EXAMPLE 1

Determination of the Tumorigenic and Metastatic Capacity

Cell line 530 was derived from a surgically removed human melanoma metastasis as described previously (van Muijen, G. N. P. et al., Clin Exp Metastasis 9 (1991) 259–272; Versteeg, R. et al., EMBO J 7 (1988) 1023–1029). Cell line NMCL-1 was also derived from a human cutaneous melanoma metastasis. Both cell lines were grown as monolayers in culture flasks in Dulbecco's modified Eagle medium supplemented with 10% fetal calf serum, glutamine, penicillin G and streptomycin. To determine the tumorigenic and metastatic capacity of the 530 and NMCL-1 cell lines, tumor cells were harvested from subconfluent cultures by 2 min treatment with 0.25% trypsin and 0.02% EDTA. After washing with serum-containing medium, the cells were suspended in PBS and $5 \times 10^6$ cells were inoculated subcutaneously (s.c.) into the lateral thoracic wall of BALB/c athymic nude mice, which were bred in the nude mouse facility of the Central Animal Laboratories, University of Nijmegen, The Netherlands. The mice were inspected twice a week for local tumor growth and general condition. Two groups of five mice each were injected for each cell line. The mice were killed when signs of illness or respiratory distress were noted. Mice that remained healthy were killed 3–4 months after inoculation. Microscopic inspection for the detection of lung metastases was performed on paraffin sections from at least 3 different levels of the lungs. Cell line 530 showed tumor take in 8 out of 10 inoculated mice. On microscopic inspection of the lungs, no metastases were found in any of these mice. Cell line NMCL-1 showed s.c. tumor growth in all 10 inoculated mice. In contrast to cell line 530, the NMCL-1 cell line showed extensive lung metastases in all mice inoculated with this cell line.

EXAMPLE 2

Differential Display PCR

Differential Display polymerase chain reaction (DD-PCR) was performed according to the method described by Liang and Pardee (Liang, P., and Pardee, A. B., Science 257 (1992) 967–971; Liang, P., et al., Cancer Res 52 (1992) 6966–6968) using the RNA image kits (GenHunter Corp., Brookline, Mass.) according to the manufacturer's recommendations. Total RNA was isolated from 530 and NMCL-1 cells by using RNeasy® Midi Kit (Qiagen, Del.). Elimination of contaminating traces of DNA from total RNA sample was performed by digestion at 37° C. for 30 min with RNase-free DNase I using the MessageClean® Kit (GenHunter Corp., Brookline, Mass.). DNA-free total RNA (0.2 µg) from 530 and NMCL-1 cells was used as a template for first strand cDNA synthesis in the presence of 3 different one-base anchored $H-T_{11}M$ primers, 1×reverse transcriptase buffer [125 mM Tris-Cl, pH 8.3, 188 mM KCl, 7.5 mM $MgCl_2$, 25 mM dithiothreitol (DDT)] and 250 µM dNTP mix. The solution was heated to 65° C. for 5 min and cooled to 37° C. for 10 min and then 200 units of Moloney murine leukemia virus (MMLV) reverse transcriptase was added. After incubation at 37° C. for 1 h, the reaction was terminated by incubation at 75° C. for 5 min. The PCR procedure was performed in solution containing 0.1 volume of reverse transcription reaction mixture, 10 µM of the respective one-base anchored $H-T_{11}M$ primer, 2 µM arbitrary 13-mer primer, 1×PCR buffer [100 mM Tris-Cl, pH 8.4, 500 mM KCl, 15 mM $MgCl_2$, 0.01% gelatin], 25 µM dNTP, 10 µCi [$\alpha$-$^{35}$S]dATP, and 10 units of AmpliTaq DNA polymerase (Perkin Elmer, Norwalk, Conn.). The PCR included a total of 40 cycles at 94° C. for 30 s, 40° C. for 2 min, 72° C. for 30 s, and finally 5 min at 72°C. After adding 2 µl loading buffer to 3.5 µl of each sample, the PCR products were heated at 80° C. for 2 min and then loaded on a denaturing 5% polyacrylamide sequencing gel for electrophoresis. The dried gel was exposed to Kodak BioMax® MR film for 48 h at room temperature and the autoradiogram was analyzed with respect to differentially expressed genes. The reaction displaying unique fragments in one of the two cell lines was subsequently confirmed by repeating reverse transcription and PCR. Unique bands reproducibly displayed in two independent DD-PCR reactions were excised from the dried gel and the cDNA was eluted from the gel by soaking the gel slice in 100 µl of $H_2O$ for 10 min and then boiling for 15 min. The cDNA was recovered by ethanol precipitation in the presence of 3M NaOAc and 50 µg glycogen as carrier and redissolved in 10 µl of $H_2O$. Four µl of eluted cDNA was reamplified in a second PCR using the same 5'- and 3'-primers and conditions described above except for dNTP concentrations of 20 µM and no radioisotope was included. The amplified PCR fragments obtained were analyzed on a 1.5% agarose gel, then purified using the QIAquick® Gel Extraction kit (Qiagen, Hilden, Del.) and used as probes for Northern analysis.

EXAMPLE 3

Sequencing and Characterization of THW Gene

Cloning of DD-PCR Fragments

Northern analysis was first performed using hybridization probes generated directly from PCR reamplification. Those amplified PCR fragments detecting differentially expressed mRNAs on a Northern blot were subcloned into the PCR 2.1-TOPO vector by the Topo TA Cloning system (Invitrogen, San Diego, Calif.). Subdoned fragments were isolated using the Qiagen plasmid kit (Qiagen) and again used as probes for Northern analysis to verify differential expression.

DNA Sequencing of Subcloned DDRT-PCR Fragments

Those subdoned fragments corresponding to mRNAs with differential expression were sequenced directly after subcloning into the Topo TA cloning vector (see above) using the Dye Terminator Cycle Sequencing kit (Applied Biosystems, Foster City, Calif.). The nucleotide sequence data were analyzed for homologies with known genes of EST's in the current DNA databases.

RT-PCR

An RT-PCR was performed to identify the 5'-extended region of the cDNA showing differential mRNA expression. The resulting 301 bp clone from the Differential Display analysis was run against EMBL Database. Full length cDNA could be obtained from the consensus sequence of 11 homologous, overlapping ESTs (Accesion Numbers: W93394, AA480373, AA610151, AA468385, R 82584, AA159815, AA159565, AI814625, AI740811, AI8300092, AI694126). The primers were designed from the resulting consensus sequence. RT-PCR was performed with the C. therm Polymerase One-Step RT-PCR System according to the manufacturer's instructions (Roche). The system is composed of an enzyme mix containing the Klenow fragment of DNA polymerase from Carboxydothermus hydrogenoformans and the thermostable Taq polymerase.

First Strand Synthesis 190 ng poly $A^+$ RNA of the cell-line 530 was reverse transcribed with the primer 312rev1 (5'AAATCCCCGAAT-TCTCCTGTGG3', SEQ ID NO:3) with a final concentration of 0.3 µM. DMSO (7%) was added in order to eliminate secondary structures at the 5'-end of the RNA due to a very high GC content (>75%). Incubation followed for 30 min at 65° C.

PCR

The PCR was performed in the same tube as the RT reaction. The first strand cDNA was used as template for the following PCR using the primer 312rev1 and primer 312f6 (5'ACCCGCTCCGCTCCGCTC3', SEQ ID NO:4) with final concentration of 0.3 µM each. PCR conditions were as follows: 35×94° C.—30 sec, 69° C.—30 sec, 72° C.—60 sec. The resulting PCR-fragment was subcloned and analyzed.

Northern Blot Analysis

Poly $A^+$ RNA was isolated from total RNA using the Oligotex® mRNA Mini Kit (Qiagen, Hilden). Parallel lanes of poly $A^+$ RNA from human melanoma cell lines, human breast carcinoma cell lines and pancreas carcinoma cell lines (1 µg of each cell line) were size-separated on a denaturing 1% agarose formaldehyde gel. Blotting to BrightStar-Plus™ (Ambion Inc., Austin, Tex.) positively charged nylon membrane was done by capillary downward transfer. After UV-crosslinking (Stratagene UV Stratalinker™ 2400) blots were hybridized to [$\alpha$-$^{32}$P]dCTP—labeled DD-PCR products prepared by random decamer (10-mer) priming and labeled to a specific activity of 2×10$^9$ cpm/µg using the Strip-EZ™ DNA Kit (Ambion Inc., Austin, Tex.). Prehybridization (0.5 h) and hybridization with radioactive probes overnight were performed in ExpressHyb™ Hybridization Solution (Clontech) at 68° C. Membranes were washed in Solution 1 (2×SSC, 0.05% SDS) at room temperature for 30–40 min with continuous agitation and several replacements of the wash solution 1 followed by a washing step with solution 2 (0.1×SSC, 0.1% SDS) at 50° C. for 40 min with one change of fresh solution. The membranes were then exposed to Cronex™ Medical X-Ray Films (Sterling Diagnostic Imaging Inc., USA) at −80° C. for 3 to 72 h. Equal loading and transfer of mRNA to the membrane was assessed by hybridizing the blots with $^{32}$P-labeled β-actin cDNA.

Multiple Tissue Expression Array and Human Tumor Panel Blot

To examine the tissue-specific expression of the THW gene, the distribution of THW mRNA in different human tissues and cell lines was analyzed by Northern blot analysis using a Multiple Tissue Expression (MTE™) Array (Clontech, Palo Alto, Calif.) and a Human Tumor Panel Blot (Invitrogen). The Tumor Panel Blot contains a panel of tumor RNA from different tissues, normal RNA is run adjacent to the tumor RNA. The MTE blot contains 76 tissue-specific polyA$^+$ RNAs. The different blots were probed with $^{32}$P-labeled THW cDNA probe. Equal loading of mRNA was verified by rehybridizing the different blots with $^{32}$P-labeled β-actin cDNA.

Sequence Analysis

The PSORT II computer program (Human Genome Center, Institute for Medical Science, University of Tokyo, Japan) was used for the prediction of protein sorting signals and localization signals in the amino acid sequence. The TMHMM (v.0.1) computer program of the Center for Biological Sequence Analysis, Department of Biotechnology (The Technical University of Denmark) was used for the prediction of transmembrane helices and their orientation in the membrane.

Figure 2:
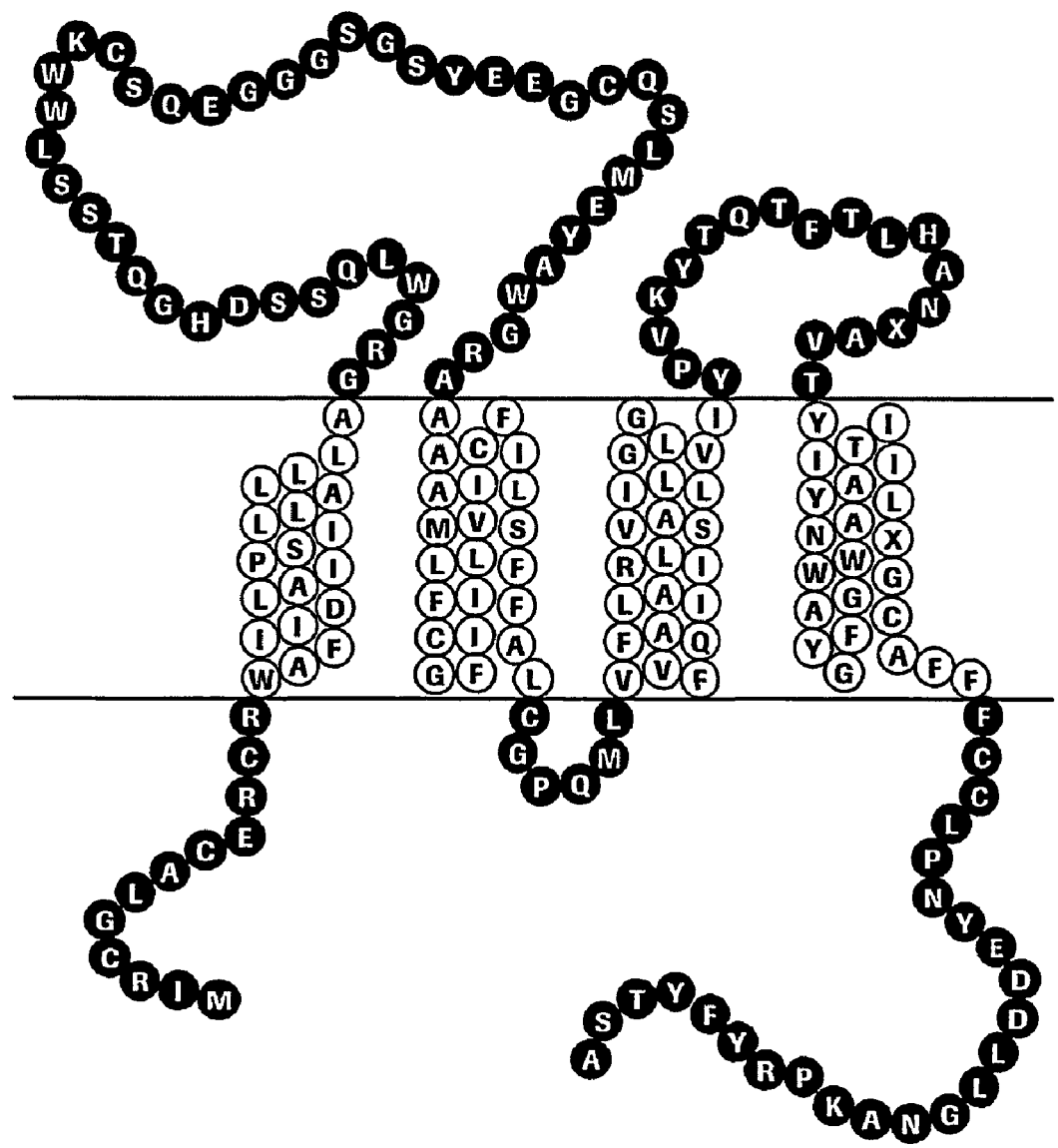
FIG. 2 Putative topology of the gene product (SEQ ID NO: 2) of the THW gene showing (from top to bottom) the extracellular, transmembrane and intracellular domains. The topology prediction is based on computer program TMHMM.

The cDNA corresponds to 1890 nts with a potential ORF of 193 aa. A polyadenylation signal was identified at nts 1855–1861. Bioinformatic-based analysis suggested a four-transmembrane receptor topology (FIG. 2). Topology of THW corresponds to a receptor with two extracellular domains (45 aa and 18 aa), four transmembrane domains (19aa, 24aa, 23aa and 23aa) and three cytoplasmic domains (12aa, 6aa and 24aa). Homologies were found on sequence comparisons with nucleotides and proteins described in WO 98/39448; WO 99/54461; WO 98/55508; and WO 99/61471.

Figure 3:
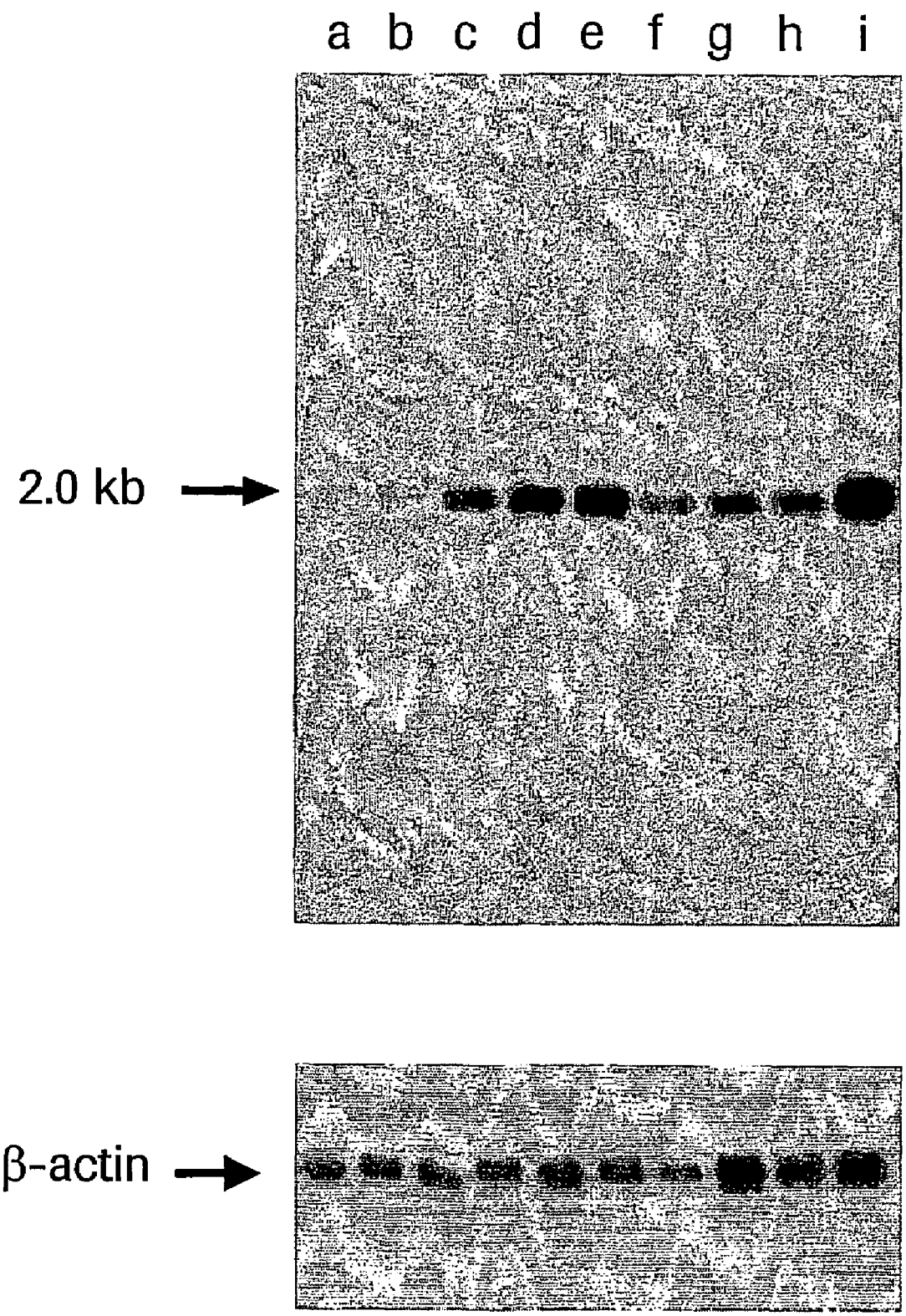
FIG. 3 Expression of mRNA for the THW gene in human melanoma cell lines with different metastatic capacity.
Northern blot was performed as described in the Materials and Methods section. The blot was hybridized with a $\alpha\text{-}^{32}$P-labelled probe derived from the THW gene. In each lane a different melanoma cell line is shown.
Lanes: a, BLM; b, MV3; c, NMCL-1 d, IF6m; e, Mel57; f, M14; g, MV-1; h, IF6; i, 530.

The correlation between the metastatic capacity of human melanoma cells in the nude mouse system and the mRNA steady-state level of the THW gene is summarized in FIG. 3. Highest steady-state level was found in the non-metastatic cell line 530 (FIG. 3, lane i), the lowest steady-state level was found in the highly metastatic cell lines BLM and MV3, as shown in lanes a and b, and intermediate levels corresponded to cell lines IF6m, NMCL-1, Mel57, M14, MV-1 and IF6 (van Muijen, G. N. P. et al., Clin Exp Metastasis 9 (1991) 259–272; Versteeg, R. et al., EMBO J 7 (1988) 1023–1029; van Muijen, G. N. et al., Int J Cancer 48 (1991) 85–91; van Groningen, J. et al., Cancer Res 55 (1995) 6237–6243; Weterman, M. A. J. et al., Cancer Res 52 (1992) 1291–1296), all of which are cell lines with intermediate potential for metastasis. These results clearly establish a correlation between down-regulation of expression of the THW gene and the metastatic potential of human melanoma cells in the nude mouse system.

Figure 4:
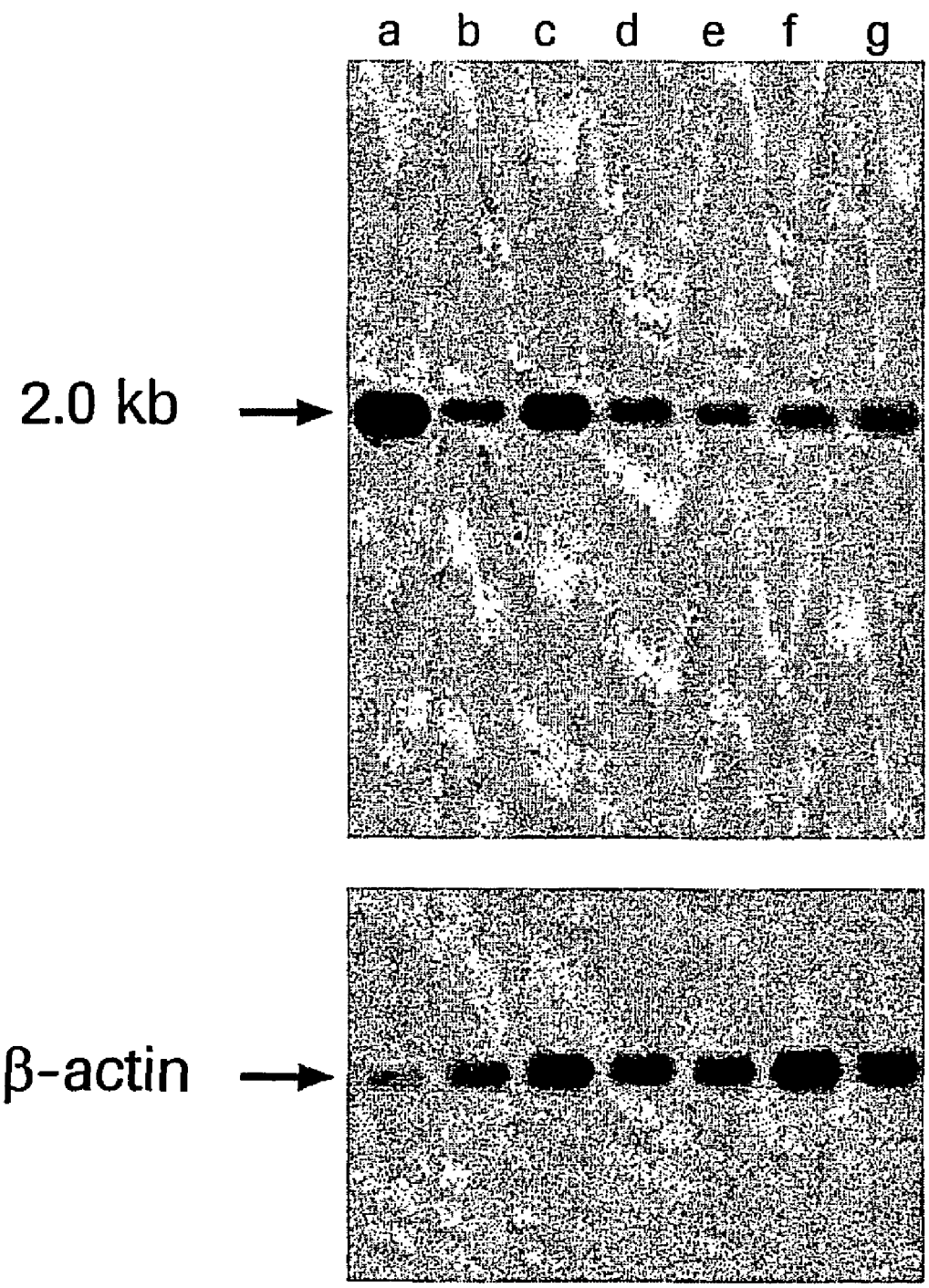
FIG. 4 Expression of the THW gene in breast carcinoma cell lines.
The cell lines are derived from normal breast epithelium (HMEC), primary mammary carcinoma (AR and WA), bone marrow micrometastases (1590, HG15 and KM22) and from ascites fluid (KS). Northern blotting was performed as described in the Materials and Methods section and the blot hybridized with an $\alpha\text{-}^{32}$P-labeled probe derived from THW cDNA.
Lane a: HMEC; b, AR; c,WA; d, 1590; e, HG15; f, KM22; g, KS.
Figure 5:
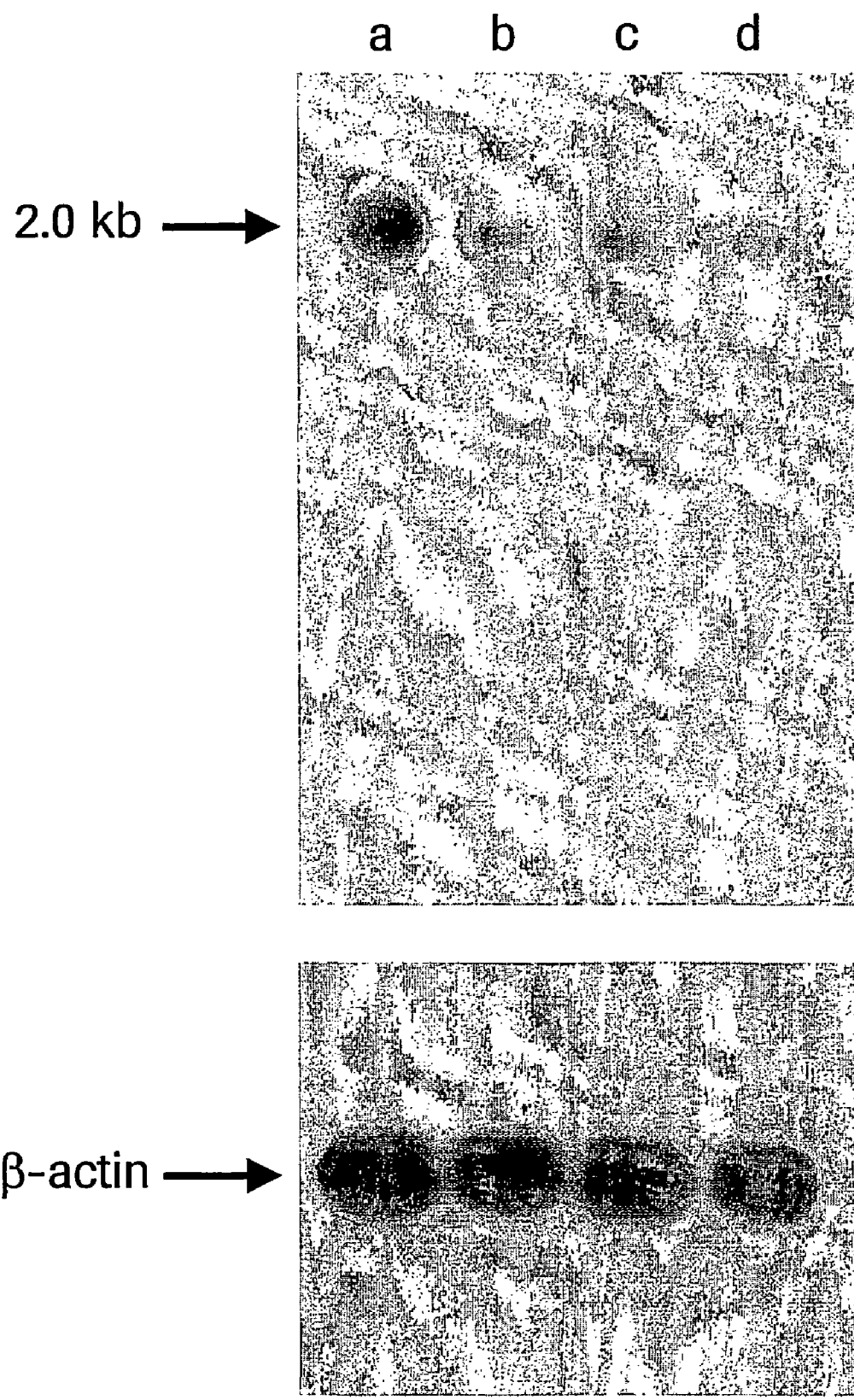
FIG. 5 Expression of the THW gene in pancreas carcinoma cell lines.
Cell line K2 is derived from a pancreas primary tumor and three cell lines (K3, K13, K16) are derived from metastases at different sites (K3 from the mesenterium, K13 from Porta hepatis and K16 from lung).
Northern blotting was performed as described in the Materials and Methods section and the blot hybridized with an $\alpha\text{-}^{32}$P-labeled probe derived from THW cDNA.
Lane a: K2; b, K3; c, K13; d, K16.

These investigations were extended to selected mammary carcinoma cell lines and their non-malignant equivalents as shown in FIG. 4. Cell lines included the normal human mammary gland epithelial cells (HMEC), cell lines derived from primary tumors (WA and AR), three cell lines derived from bone marrow micrometastases of mammary carcinoma (KM22, HG15 and 1590) and one cell line derived from ascites (KS). With the exception of cell line WA (FIG. 4, lane c), all other mammary carcinoma cell lines (FIG. 4, lanes a, b, c, d, f) exhibited significant (10-fold) down-regulation of the steady-state level of the mRNA of the THW gene. These results indicate that down-regulation of expression of the THW gene plays a role in the pathogenesis of mammary carcinoma as well. Similar results were found within a panel of cell lines established from an orthotopic xenograft mouse model. One cell line (K2) was derived from a primary tumor and three cell lines were derived from metastases at different sites (K3 from the mesentery, K13 from the porta hepatis, K16 from the lungs). As shown in FIG. 5, THW mRNA was downregulated in all three cell lines derived from metastases (K3, K13, K16) compared with the cell line derived from the primary tumor (K2).

Figure 6:
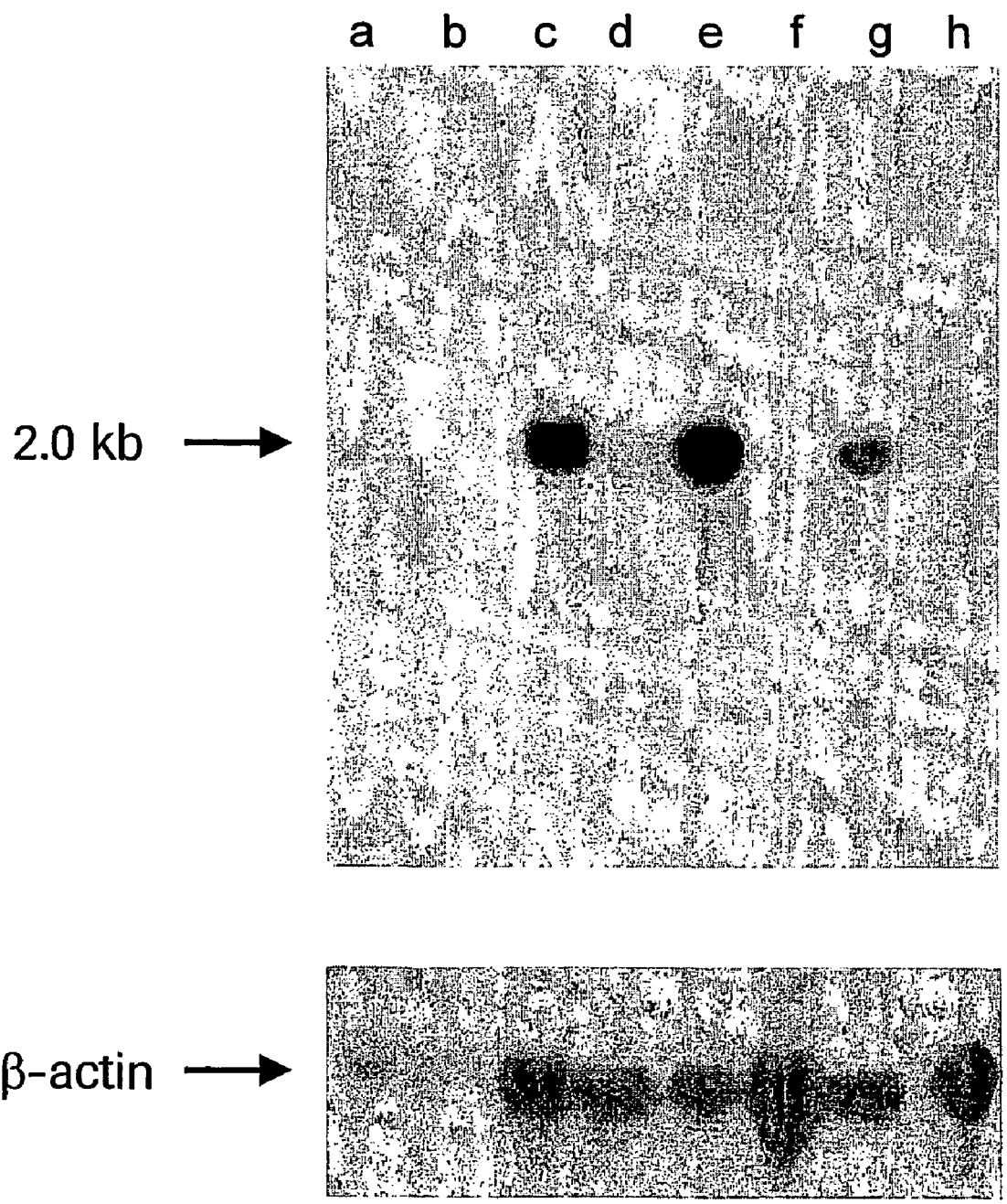
FIG. 6 Expression of THW in selected tumors and their corresponding normal tissues.
Northern blot analysis was performed as described in the Materials and Methods section. The blot was hybridized to an $\alpha\text{-}^{32}$P-labeled cDNA derived from THW cDNA.
Lane a: normal ovary; b: ovarian tumor; c: normal cervix; d, cervical cancer; e: normal uterus; f: uterine tumor; g: normal breast; h: breast tumor.

The steady-state level of THW mRNA in several tumor samples (breast, uterus, cervix and ovarian carcinomas) was compared with the corresponding normal tissues as outlined in FIG. 6. In breast, uterine and cervical carcinomas dramatically reduced mRNA levels of THW were found in comparison with the corresponding normal tissues; in ovarian carcinoma, no signal was detected in either normal or tumor tissue. These experiments indicate downregulation of the THW gene in some solid tumors.

Figure 7:
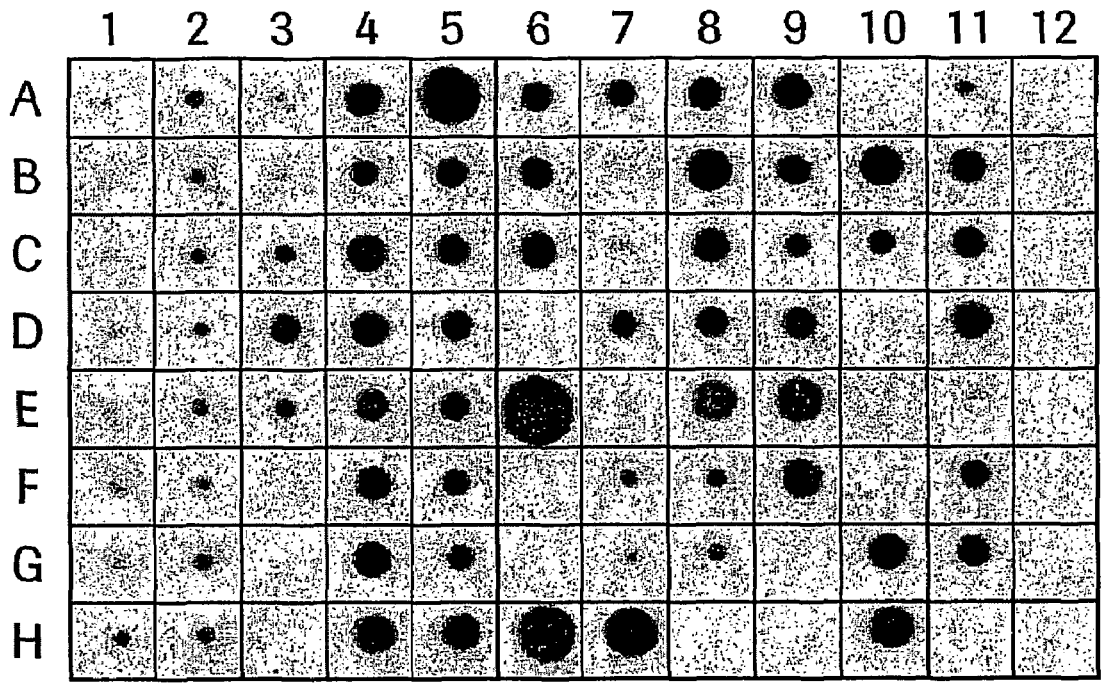
FIG. 7 Expression of the THW gene in selected tissues and cell lines.
The Multiple Tissue (MTE™) Array (Clontech, Palo Alto, Calif. ) was hybridized with an $\alpha\text{-}^{32}$P-labeled probe corresponding to THW cDNA according to the recommendations of the manufacturer. E6 corresponds to 1 µg poly A$^+$RNA from cell lines AR, H6 corresponds to 0.1 µg poly A$^+$RNA from cell line AR. The coding is revealed above the blot.
A1=whole brain; A2=cerebellum, left; A3=substantia nigra;
A4=heart; A5=esophagus; A6=colon, transverse; A7=kidney,
A8=lung; A9=liver; A10=leukemia, HL-60; A11=fetal brain;
A12=yeast total RNA.
B1=cerebral cortex; B2=cerebellum, right; B3=accumbens nucleus; B4=aorta; B5=stomach; B6=colon, descending;
B7=skeletal muscle; B8=placenta; B9=pancreas; B10=HeLaS3;
B11=fetal heart; B12=yeast tRNA.

Expression of the THW gene in normal and selected fetal tissues as well as selected tumor cell lines was investigated by making use of multiple tissue expression array (MTE™, Clontech) as shown in FIG. 7. THW was expressed in tumor cell lines such as HeLa, colorectal adenocarcinoma cell line SW480 and lung carcinoma cell line A549, but was very weakly expressed in erythroleukemic cell line K562 and not expressed in other hematopoietic tumor cell lines such as leukemia cell lines Molt4, leukemia HL-60 and Burkitt's lymphoma cell lines Raji and Daudi. No expression could be detected in peripheral blood leukocytes and only very weak expression was found in brain and its compartments, skeletal muscle, spleen, lymph node, bone marrow, testis and ovary. Intermediate expression was found in the heart and its compartments, gastrointestinal organs, kidney, thymus, lung, bladder, placenta, uterus, liver, pancreas, adrenal gland, thyroid gland, salivary glands, prostate and mammary glands; high expression was found in the esophagus and trachea. THW was expressed in fetal heart, kidney, liver, thymus and lung and only very weakly in fetal brain and spleen. THW is thus almost ubiquitously expressed with exception of peripheral blood leukocytes. The receptor is ubiquitously expressed with the exception of peripheral blood leukocytes (FIG. 7).

The tumor-suppressor function of THW is therefore characterized by the following findings:

a) Down-regulation of the THW gene in metastasizing human melanoma cells compared with intermediate and non-metastasizing cell lines in the nude mouse system (FIG. 3)

b) Down-regulation of the THW gene in mammary carcinoma cell lines compared with human mammary gland epithelial cells (FIG. 4)

c) Down-regulation of the THW gene in pancreas cell lines derived from metastases compared with a cell line derived from a primary tumor (FIG. 5).

d) Down-regulation of the THW gene in tumor tissue compared with normal tissue (FIG. 6)

EXAMPLE 4

Detection of LOH

Microsatellites are short sequences (50–300 bp) composed of tandemly repeated monomers (1–6 bp) These microsatellites are widespread throughout the genome and many of them are highly polymorphic. Polymerase chain reaction (PCR) analysis was used to study the incidence of allelic loss at 6q24 of various cell lines and tumor biopsies. For this propose, oligonucleotides flanking three polymorphic microsatellite markers were used. All of them were dinucleotide repeats.

Pairs of normal DNA and autologous tumor DNA (primary melanomas and metastatic melanoma) from 35 patients were analyzed, using a panel of three polymorphic DNA markers localized to the long arm of chromosome 6. There were also analyzed various human melanoma, breast, cervix, prostate and ovary carcinoma cell lines.

LOH is defined as >50% loss in relative peak height of a tumor allele compared to the normal allele.

We used the following formula to calculate the LOH:

$$LOH = \frac{(\text{peak height of normal allele 2}/\text{peak height of normal allele1})}{(\text{peak height of tumor allele 2}/\text{peak height of tumor allele1})}$$

Allelic loss is indicated by an LOH value less than 0.5 or higher than 2.0.

a) DNA extraction

High molecular weight DNA was isolated from 25 primary melanomas and 10 melanoma metastases. The DNA was isolated from (micro)dissected paraffin sections. DNA was also isolated from normal tissue from the same patients. DNA from tumor cell lines was extracted from pelleted cells. The DNA was isolated using the QIAamp® (Qiagen, Del.) DNA Mini Kit.

b) PCR analysis

Fluorescence labeled primers flanking highly polymorphic dinucleotide repeats at D6S292, D6S1684 and D6S311.

| Intervall | Locus | Marker | Hetero-zygosity | Sequence forward Modification | Sequence reverse | Product |
|---|---|---|---|---|---|---|
| D6S472–D6S453 | D6S292 | AFM203za9 | 0.834 | tccttcccacctcccttct (SEQ ID NO:5) 5'6-FAM | Taagaactaaagttgcctgttc (SEQ ID NO:6) | 106 |

-continued

| Intervall | Locus | Marker | Hetero-zygosity | Sequence forward Modification | Sequence reverse | Product |
|---|---|---|---|---|---|---|
| D6S472–D6S453 | D6S1684 | AFM360th9 | 0.8 | caactggattcaaaatagatgtc (SEQ ID NO:7) 5'HEX | Atggcagcaggctatgt (SEQ ID NO:8) | 247 |
| D6S453–D6S311 | D6S311 | AFM276xf1 | 0.92 | Atgtcctcattggtgttgtg (SEQ ID NO:9) 5'HEX | Gattcagagcccaggaagat (SEQ ID NO:10) | 259 |

PCR conditions were as follows:

Set up Master Mix 1:

| Component | Vol. | Final conc. |
|---|---|---|
| Forward primer | 1 µl | 300 nM |
| Reverse primer | 1 µl | 300 nM |
| Template DNA | X µl | 50–100 ng |
| Sterile water, PCR grade | Up to 25 µl | |

Master Mix 2:

25 µl High Fidelity PCR Master (Roche Diagnostics GmbH, DE)

Pipet both mixes together. PCR was carried out using the following cycles: 2 min 94° C. and 40×94° C.—30 sec, 55° C.—30 sec, 72° C.—30 sec with a final extension of 7 min at 72° C. The three primer pairs generate flourescence labeled PCR products for analysis on the ABI PRISM 310 Genetic Analyzer with the GeneScan Analysis Software (PE Applied Biosystems).

List of References

Ausubel I., Frederick M., Current Protocols in Mol. Biol. (1992), John Wiley and Sons, New York
Bilanges, B. et al., Oncogene 18 (1999) 3979–3988
Boraschi, D., et al., Cell Immunol. 45 (1979) 188–194
Boraschi, D., et al., J. Immunol. 131 (1983) 1707–1713
Büttner, R., et al., Mol. Cell. Biol. 11 (1991) 3573–3583
Chappell, S. A. et al., British J Cancer 75 (1997) 1324–1329
Chen, Y. H., et al., J. Pathol. 177 (1995) 129–134
de la Chapelle, A., Eur. J. Hum. Genet. 7 (1999) 407–408
Devilee, P., et al., Oncogene 6 (1991) 1705–1711
Dockhorn-Dworniczak, B., et al., Virchows Arch. 424 (1994) 337–342
EP-A 0 063 879
EP-A 0 173 251
EP-A 0 200 362
Fidler, I. J., Cancer Metastasis Rev 50 (1986) 29–49
Friedrich, M. G., et al., J. Urol. 163 (2000) 1039–1042
Fujii, H., et al., Genes, Chromosomes & Cancer 16 (1996) 35–39
Griffin, C. A. et al., Cancer Research 55 (1995) 2394–2399
Gruis, N. A., et al., Br. J. Cancer 68 (1993) 208–213
Hahn, M., et al., BioTechniques 18 (1995) 1040–1047
Hames, B. D., Higgins, S. G., Nucleic Acid Hybridisation—A Practical Approach (1985) IRL Press, Oxford, England
Healy, E. et al., Oncogene 16 (1998) 2213–2218
Huettner, P. C. et al., Human Pathol 29 (1998) 364–370
Liang, P. and Pardee, A. B., Science 257 (1992) 967–971
Liang, P., et al., Cancer Res 52 (1992) 6966–6968
Lin, R. J. et al., Trends Genet 15 (1999) 179–184
Lopez-Crapez, E., et al., BioTechniques 17 (1994) 1072–1074, 1076
MacGrogan, D. and Bookstein, R., Seminars in Cancer Biology 8 (1997) 11–19
Merlo, G. R., et al., BioTechniques 11 (1991) 166–168, 170–171
Millkin, D. et al., Cancer Research 51 (1991) 5449–5453
Noviello, C. et al., Clin Cancer Research 2 (1996) 1601–1606
Pardee, A. B., Advances in Cancer Res 65 (1994) 213–227
Ponta, H., Biochim Biophys Acta 1198 (1994) 1–10
Potocnik U. et al., Pflügers Arch 439 ($3^{rd}$Suppl.) (2000) R47–9
Ray, M. E. et al., Oncogene 12 (1996) 2527–2533
Robertson, G. P. et al., Cancer Res 56 (1996) 1635–1641
Sambrook et al., Molecular Cloning: A Laboratory Manual (1989), Cold Spring Harbor Laboratory Press, New York, USA
Schiemann, S. et al., Anticancer Research 17 (1997) 13–20
Schiemann, S. et al., Clin Exp Metastasis 16 (1998) 129–139
Schwirzke, M. et al., Anticancer Res 19 (1999) 1801–1814
Schwirzke, M. et al., Anticancer Research 18 (1998) 1409–1422
Srikantan, V. et al., Int J Cancer 84 (1999) 331–335
Stunnenberg, H. G. et al., Biochem Biophys Acta 1423 (1999) F15-F33
Sugano, K., et al., Genes, Chromosomes & Cancer 15 (1996) 157–164
Trent, J. M. et al., Science 247 (1990) 568–71
U.S. Pat. No. 2,915,082
van Groningen, J. et al., Cancer Res 55 (1995) 6237–6243
van Muijen, G. N. et al., Int J Cancer 48 (1991) 85–91
van Muijen, G. N. P. et al., Clin Exp Metastasis 9 (1991) 259–272
Verma, R. S. et al., Cancer Investigation 17 (1999) 441–447
Versteeg, R. et al., EMBO J 7 (1988) 1023–1029
Wahl, G. M., et al., Proc. Natl. Acad. Sci. USA 76 (1979) 3683–3687
Weterman, M. A. J. et al., Cancer Res 52 (1992) 1291–1296
WO 89/06698
WO 98/39448
WO 98/55508
WO 99/54461
WO 99/61471

The invention claimed is:

1. A process to screen a test sample containing cells for potentials to develop tumor, tumor progression or metastasis, against a base sample, the process comprises the following steps:
  (a) incubating the test sample and the base sample under hybridization conditions with a nucleic acid probe selected from the group consisting of:
    (i) a nucleic acid sequence of SEQ ID NO:1;
    (ii) a nucleic acid sequence which is complementary to any nucleic acid sequence of (i);
    (iii) a nucleic acid sequence which hybridizes under stringent conditions with the sequence of (i); and
    (iv) a nucleic acid sequence which hybridizes under stringent conditions with the sequence of (ii);
  (b) determining the amount of hybridization of the test sample and the base sample with said probe; and
  (c) comparing the amount of hybridization of the test sample to an amount of hybridization of said base sample: wherein if the amount of hybridization of the test sample is less than the amount of hybridization of the base sample, the cells in the test sample have a greater potential for developing or progressing tumors or metastasis than the cells in the base sample.

2. The process according to claim 1 wherein the test sample originates from or contains human cells.

3. The process according to claim 1 wherein the base sample originates from non-tumor cells obtained from human cells.

4. The process according to claim 1 wherein the hybridization proceeds under stringent conditions.

* * * * *